United States Patent [19]

Nishikawa et al.

[11] Patent Number: 5,340,544
[45] Date of Patent: Aug. 23, 1994

[54] PLUG-OPENING DEVICE FOR A SPECIMEN CONTAINER

[75] Inventors: Susumu Nishikawa; Hariko Ikuma, both of Hamamatsu, Japan

[73] Assignee: System Stack Co., Ltd., Hamana, Japan

[21] Appl. No.: 45,735

[22] Filed: Apr. 14, 1993

[30] Foreign Application Priority Data

Jun. 22, 1992 [JP] Japan .................................. 4-187595

[51] Int. Cl.⁵ .......................... B01L 11/00; B67B 7/02
[52] U.S. Cl. ....................................... 422/99; 81/3.2; 81/3.55
[58] Field of Search ............... 422/99, 63; 81/3.07, 81/3.08, 3.2, 3.55

[56] References Cited

U.S. PATENT DOCUMENTS

| | | | |
|---|---|---|---|
| 854,812 | 5/1907 | Dodge | 81/3.07 |
| 1,890,882 | 12/1932 | Murray | 267/165 |
| 2,029,804 | 2/1936 | Williamson | 81/3.08 |
| 3,628,405 | 12/1971 | Fleisher | 81/3.42 |
| 4,135,883 | 1/1979 | McNeil et al. | 422/72 |
| 4,217,798 | 8/1980 | McCarthy et al. | 81/3.2 |
| 4,869,133 | 9/1989 | Irazoqui et al. | 81/3.08 |
| 5,008,082 | 4/1991 | Shaw | 422/63 |
| 5,080,864 | 1/1992 | Shaw | 422/62 |
| 5,138,891 | 8/1992 | Johnson | 73/864.67 |

Primary Examiner—Robert J. Warden
Assistant Examiner—Robert Carpenter
Attorney, Agent, or Firm—Armstrong, Westerman, Hattori, McLeland & Naughton

[57] ABSTRACT

A plug-opening device which includes a rod capable of moving forwards or backwards, and a plug-opening member having elastic leaf springs, for urging against a circumferential side of a plug of a specimen container, attached to the rod in the longitudinal direction. The plug-opening member preferably includes a plurality of leaf springs in a stack formation, wherein an end portion of a higher leaf spring relative to another end portion of a lower leaf spring, adjacent to the higher leaf spring, extends further away from the end portion of the rod. More preferably, the plurality of leaf springs are attached with a gap being formed between upper and lower leaf springs. The plug-opening device can reliably, effectively, and smoothly open a plug of a specimen container with one stroke of the cylinder rod.

2 Claims, 3 Drawing Sheets

PLUG-OPENING DEVICE FOR A SPECIMEN CONTAINER

BACKGROUND OF THE INVENTION

1. Field of the Invention

The present Invention concerns a plug-opening device For a specimen container containing blood or like other specimen and tightly sealed with a plug, wherein the plug is for example, made of rubber.

2. Description of the Prior Art

A specimen, such as blood, sampled from a human body is sealed in a container such as a test tube, and sampling is conducted upon inspection by removing the plug out of the container.

In recent years, specimens have been handled very carefully for preventing the spread of infectious diseases. In a known plug-opening device for contactless treating of specimens, a rigid rod is attached to a top end of a cylindrical rod that reciprocates forward and backward and a top end of a plug-opening member is caused to abut obliquely and upwardly against the circumferential side of a plug of a specimen container for extracting the plug.

However, since the conventional device for opening the plug of this kind has a structure for opening the plug by urging the top end of a rigid rod, the rod is fully extended in its opening-stroke before the plug is opened completely, or the rod is detached from the plug, so that the specimen container not yet opened is forwarded in its unopened state to a sampling line. For preventing this, the plug-opening operation has to be conducted over and over, but this option is extremely inefficient.

OBJECT OF THE INVENTION

It is, accordingly, an object of the present invention to provide a device for opening a plug which is capable of reliably and smoothly opening a plug from a specimen container by the opening-stroke of a cylinder rod within about one operation.

SUMMARY OF THE INVENTION

The foregoing object can be attained in accordance with the present invention by a plug-opening device comprising a rod capable of moving forward and backward, and a plug-opening member comprising elastic leaf springs urged against the circumferential side of a plug of a specimen container attached to the rod in the longitudinal direction.

In a preferred embodiment, a plug-opening member comprises a plurality of leaf springs which are attached in multistages with a top end of a lower leaf spring being retreated from the top end of an upper leaf spring adjacent thereto.

In a further preferred embodiment, a gap is formed between each of the upper and lower leaf springs in the plug-opening member.

Since the plug-opening member at the top end of the cylinder rod comprises the leaf spring that is bent elastically, the top end of the leaf spring effectively follows after the plug that deforms and displaces during the plug-opening operation, and it does not detach even when the opening stroke reaches its maximum length. Accordingly, the plug can be pushed out of the container by a single stroke.

In the preferred embodiment of the present invention, the longest uppermost leaf spring is at first urged against the circumferential side of the plug in the opening stroke of advancing the cylinder rod, thereby raising the plug.

Then, as the opening-stroke travels further, the leaf springs at the uppermost stage and the succeeding stage cooperatively raise the plug at its different positions. Even when the top end of the uppermost leaf spring detaches from the plug, since the leaf spring at the next stage still raises the plug, the plug-opening operation is continuous.

When the plug-openings operation is transferred as far as the leaf spring at the lowest stage, the plug can surely be pulled out of the single specimen container by the opening stroke.

In the further preferred embodiment, since the gap is formed between the upper and the lower leaf springs, the leaf springs do not interfere with each other and individual springs function independently.

BRIEF DESCRIPTION OF THE DRAWINGS

These and other objects, as well as advantageous features of the present invention, will become more apparent from the following description of preferred embodiments with reference to the accompanying drawings, wherein.

DESCRIPTION OF PREFERRED EMBODIMENTS

Description will be made to the preferred embodiments according to the present invention with reference to the accompanying drawings.

Figure 1:
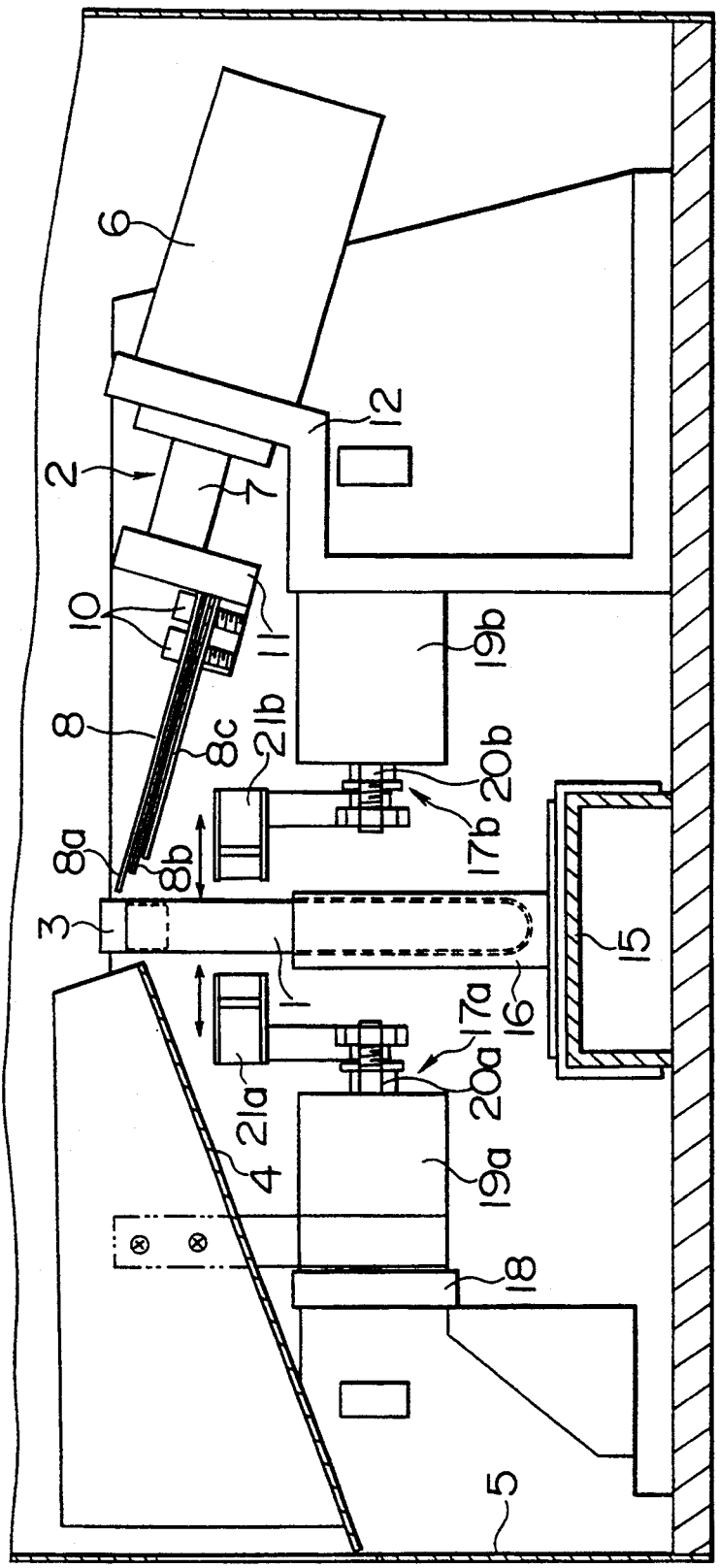
FIG. 1 is a schematic view for the entire structural of an apparatus for opening a plug by using plug-opening device according to the present invention.

FIG. 1 illustrates the entire constitution of an apparatus for opening a plug of a specimen container by using a plug-opening device in accordance with the present invention. Shown in FIG. 1 is a specimen container 1 which is brought into a line for opening a plug or cork of the specimen container, a plug-opening device 2 according to the present invention disposed to a plug or cork 3 of the specimen container 1, and a hopper 4 for receiving a detached plug 3 and sending it out of a casing 5.

Figure 2:
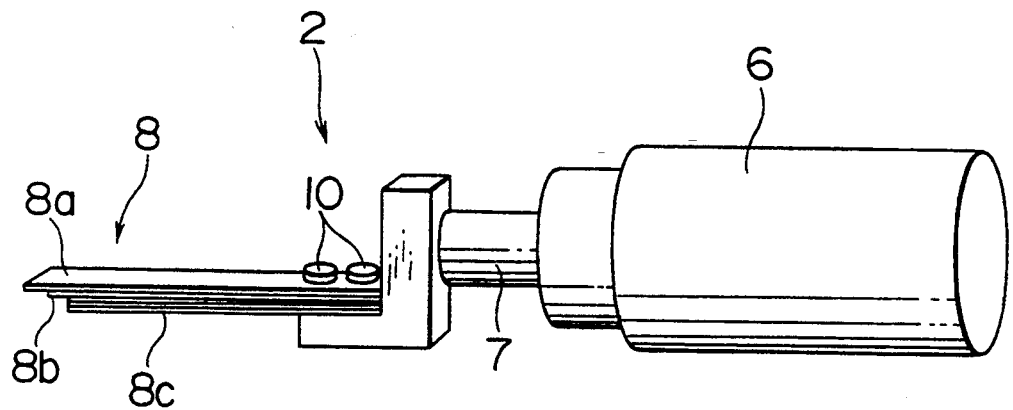
FIG. 2 is a side elevational view of the plug-opening device in a preferred embodiment according to the present invention.

As shown in FIG. 1 and FIG. 2, a plug-opening device 2 has a cylinder 6 having a rod 7 that reciprocates forward and backward, and a plug-opening member 8 which is made of an elastically bending leaf spring attached to the top end of the rod 7 in the longitudinal direction.

The plug-opening member 8 may include a single leaf spring; and, in a more preferred embodiment shown in the drawing, three leaf springs 8a, 8b and 8c are stacked one above the other such that the top end of a lower leaf spring is somewhat retreated from the top end of an upper leaf spring adjacent thereto.

A protruding length, that is, a longitudinal difference between the leaf springs 8a and 8b and between the leaf springs 8b and 8c is properly determined depending on the shape, the size or the like of the plug to be opened.

Preferably, attaching ends of the leaf springs 8a, 8b and 8c are detachably secured by means of bolts 10 to a base member 11 at the top end of the rod 7 as shown in the drawing, so that the protruding length between the top ends of the upper and the lower leaf springs can be adjusted as required.

Each of the leaf springs 8a8b and 8c is made of a metal or plastic plate which has a mechanical strength upon pushing forward, and is elastically bendable, so that a leaf spring urged against the plug 3 upon plug-opening operation gives an upwardly force to the plug, while being elastically distorted.

In a more preferred embodiment, the leaf springs may be attached with a gap being formed between each of adjacent leaf springs.

Figure 3:
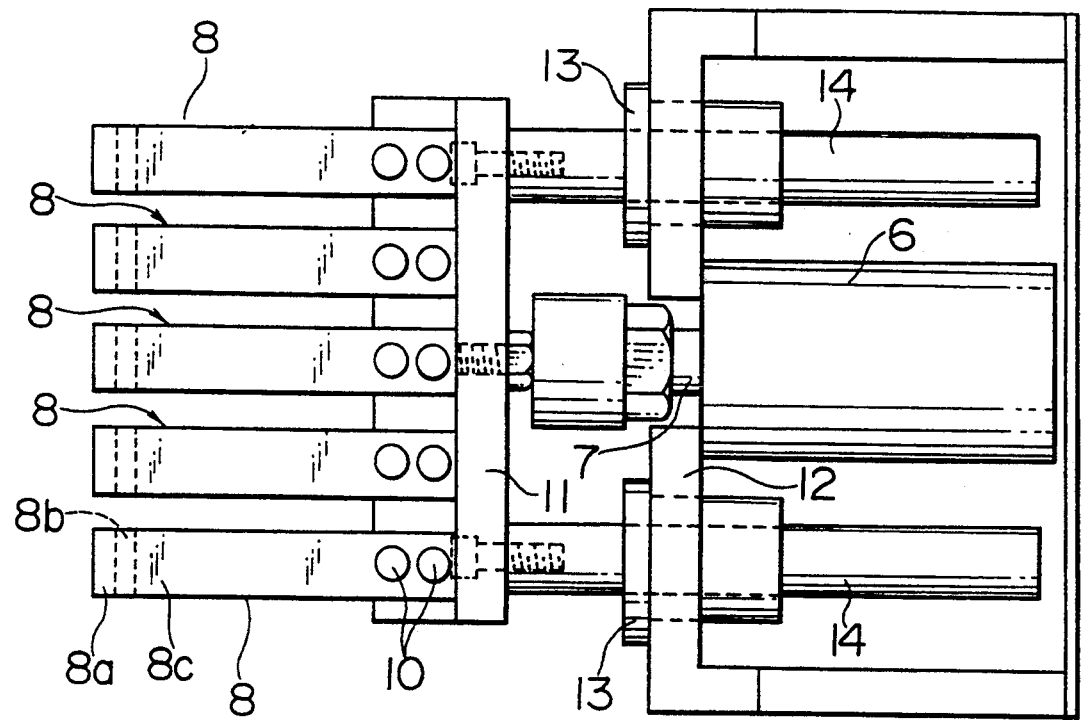
FIG. 3 is a plan view of the plug-opening device in another preferred embodiment.

Basically, the leaf spring plug-opening member 8 may be disposed only by one set to the cylinder rod 7 as shown in FIG. 1. Preferably, five sets of plug-opening members 8 arranged in parallel with each other are attached to a base member 11 at the top end of the cylinder rod 7, as shown in FIG. 3, so that plugs of five specimen containers 1 can be opened at the same time.

Preferably, in this modified embodiment, guide members 13 and 13 are disposed to a support bracket 12 of the cylinder 6, guide bars 14 and 14 are attached to the base member 11 for attaching the plug-opening member 8, and the guide bars 14 slidably pass through the guide members respectively, so that the five sets of plug-opening members 8 move forward and backward in a stable manner.

As shown in FIG. 1, the specimen container 1 is contained with a lower half portion thereof and is inserted in a holding case 16 which is transported along a guide rail 15. The container 1 is transported in this state to a plug-opening position between the plug-opening device 2 and the plug receiving hopper 4.

As shown in FIG. 1, the plug-opening device 2 is secured to the support bracket 12 such that the top end of the plug-opening member 8 is obliquely opposed from below to the plug 3 of the specimen container 1 which stops at the plug-opening position.

It will be apparent that in a case where the plug-opening device 2 has five sets of the plug-opening members 8 as shown in FIG. 3, five specimen containers 1 are contained in five containing portions of a holding case 16, respectively, so that each of the plug-opening members 8 and each of the specimen containers I are opposed to each other correspondingly.

In FIG. 1, chuck devices 17a and 17b are secured to brackets 12 and 18 situated on both right and left sides of the plug-opening position. The chuck devices 17a and 17b comprise cylinders 19a and 19b secured to the bracket 12 and 18 and have cylinder rods 20a and 20b, and bifurcate chuck members 21a and 21b secured at the top ends of the cylinder rods 20a and 20b, such that the chuck members 21a and 21b on the right and left approach and hold the circumferential periphery of the specimen container 1 from both sides upon opening the plug.

Thus, when the specimen container 1 is sent to the plug-opening position, the chuck members 21a and 21b hold the specimen container 1 from both sides to restrict its upward movement.

Then, the leaf spring 8a of the plug-opening member 8 of the plug-opening device 2 is urged against the plug 3 placed in the specimen container 1 and raises the specimen 3 obliquely from below by an extending stroke of the cylinder 7.

The leaf spring plug-opening member 8 keeps urging the plug 3 following the movement of the specimen by its elastic distortion until the plug 3 is extracted.

Figure 4A:
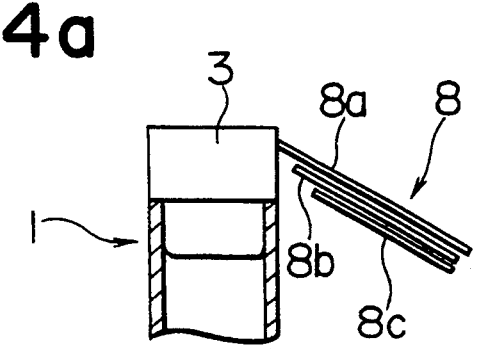
FIGS. 4a, 4b and 4c are explanatory views for the operation of the plug-opening device according to the present invention.
Figure 4B:
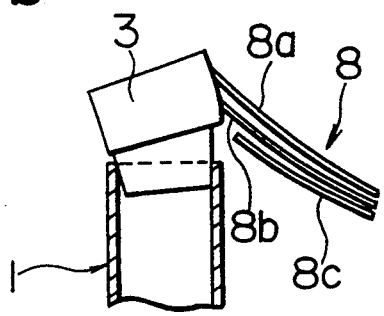
Figure 4C:
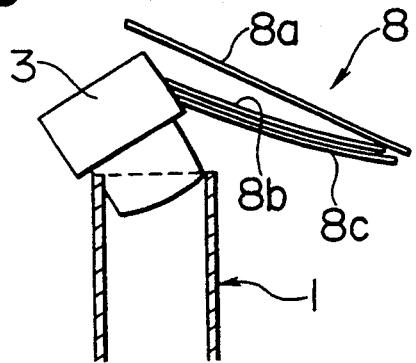

In a case where the plug-opening member 8 comprises a plurality (three) of leaf springs 8a, 8b and 8c with the top ends thereof being retreated successively, as shown in FIG. 4a through 4c, after the upper leaf spring 8a conducts initial plug-opening operation to the plug 3, the leaf spring 8b at the succeeding stage urges against the lower circumferential side of the plug 3 to push it upward. In the same sequence, when the lowermost leaf spring 8c raises the plug 3, the plug 3 completely detaches from the main body of the container 1 and is discharged from the hopper 4.

In accordance with the present invention, since the plug-opening member of the plug-opening device is constituted with leaf springs having a mechanical strength and bending elastically, the leaf springs can follow after the movement of the plug body upon opening of the plug and, therefore, the plug can be extracted completely by one opening-stroke. Accordingly, the efficiency of the plug-opening operation can be improved remarkably.

In particular, since a plurality of leaf springs are disposed in multistages with their top ends being retreated successively, a plurality of leaf springs raise the plug at its different positions, so that the plug can be smoothly opened in a stable state. In addition, even if a leaf spring at the upper stage detaches from the plug, since a leaf spring at the lower stage functions as a back up, the reliability in the plug-opening step can further be insured.

The above description is included to illustrate the preferred embodiments and the operations thereof, and is not intended to limit the scope of the invention. The scope of the invention is to be limited only by the following claims. From the above discussion, many variations are apparent to one skilled in the art which would yet be encompassed by the spirit and scope of the invention.

What is claimed is:

1. A plug-opening device, comprising:
   a rod;
   actuating means, coupled to said rod, for actuating the rod away from or towards a plug of a specimen container; and
   a plug-opening means, coupled to an end portion of the rod and extended from the rod at a longitudinal direction thereof, for urging against a circumferential side of the plug, wherein the plug-opening means comprises elastic leaf springs urged against the circumferential side of the plug of the specimen container,
   wherein said elastic leaf springs include a plurality of plug-opening leaf spring members which are attached to the end portion of the rod in a stack formation, and wherein an end portion of a higher leaf spring relative to another end portion of a lower leaf spring, adjacent to the higher leaf spring, extends further away from the end portion of the rod.

2. A plug-opening device as defined in claim 1, wherein the upper and lower leaf springs have a gap therebetween.

* * * * *

UNITED STATES PATENT AND TRADEMARK OFFICE
CERTIFICATE OF CORRECTION

PATENT NO. : 5,340,544
DATED : Aug. 23, 1994
INVENTOR(S) : Susumu Nishikawa, et al It is certified that error appears in the above-indentified patent and that said Letters Patent is hereby corrected as shown below:

On cover page, item [75] "Hariko" should read --Mariko--.

Signed and Sealed this

Eighth Day of November, 1994

Attest:

BRUCE LEHMAN

*Attesting Officer*      *Commissioner of Patents and Trademarks*